United States Patent [19]

Kühle et al.

[11] Patent Number: 4,798,905
[45] Date of Patent: Jan. 17, 1989

[54] SULPHENYLATED CARBAMIC ACID ESTERS, A PROCESS FOR THEIR PREPARATION AND THEIR USE

[75] Inventors: Engelbert Kühle, Bergisch Gladbach; Wilfried Paulus; Hermann Genth, both of Krefeld; Paul Reinecke; Gerd Hänssler, both of Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 87,056

[22] Filed: Aug. 18, 1987

Related U.S. Application Data

[63] Continuation of Ser. No. 734,924, May 16, 1985, abandoned.

[30] Foreign Application Priority Data

May 17, 1984 [DE] Fed. Rep. of Germany ....... 3418375

[51] Int. Cl.$^4$ ............................................. C07C 145/04
[52] U.S. Cl. ...................................... 560/16; 558/412; 558/417
[58] Field of Search ................... 560/16; 514/487, 484, 514/486, 488

[56] References Cited

U.S. PATENT DOCUMENTS

| | | | |
|---|---|---|---|
| 3,890,386 | 6/1975 | Kuhle | 564/102 |
| 3,906,024 | 9/1975 | Moore | 564/97 |
| 4,005,141 | 1/1977 | Moore | 564/97 |
| 4,312,663 | 1/1982 | Mikhail | 71/88 |
| 4,405,359 | 9/1983 | Mikhail | 71/103 |

FOREIGN PATENT DOCUMENTS

| | | | |
|---|---|---|---|
| 13759 | 12/1979 | European Pat. Off. | 560/16 |
| 1493581 | 9/1981 | France . | |
| 1940625 | 2/1971 | Fed. Rep. of Germany | 560/16 |

Primary Examiner—Michael L. Shippen
Attorney, Agent, or Firm—Sprung Horn Kramer & Woods

[57] ABSTRACT

The new sulphenylated carbamic acid esters of the formula

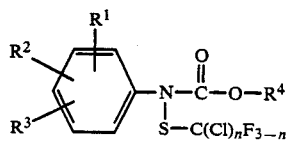

in which
R$^1$ to R$^3$ are identical or different and denote hydrogen, halogen, nitro, cyano, alkyl, alkoxy, alkylmercapto, trihalogenomethyl, trihalogenomethoxy or trihalogenomethylmercapto,
R$^4$ represents an optionally substituted alkyl, alkenyl, alkinyl, cycloalkyl or aralkyl radical and
n represents one of the numbers 0, 1, 2 or 3, can be prepared by reacting the corresponding N-substituted carbamic acid fluorides with an alcohol. They are active compounds for combating microorganisms.

5 Claims, No Drawings

SULPHENYLATED CARBAMIC ACID ESTERS, A PROCESS FOR THEIR PREPARATION AND THEIR USE

This is a continuation of application Ser. No. 734,924, filed May 16, 1985, now abandoned.

This invention relates to new N-sulphenylated carbamic acid esters, a process for their preparation, microbicidal agents containing these compounds and their use as microbicides, in particular for preserving industrial materials and in plant protection.

The use of some N-(trihalogenomethylthio) compounds for preserving industrial materials from microbial degradation is known (U.S. Pat. No. 2,563,770, Journ. Agr. Food Chem. 14, 365 (1966) and Fette, Seifen, Anstrichmittel 68, 272 (1966)). However, they are not always satisfactory, since not all microorganisms are affected by them; in addition, they have a poor solubility in paints and impregnating agents.

It is also known that N-(trihalogenomethylthio) compounds can be used as fungicides in agriculture and horticulture. Thus, for example, N-(trichloromethylthio)tetrahydrophthalimides (German patent specification No. 887,506) and N,N-dimethyl-N'-phenyl-N'-(fluorodichloromethylthio)-sulphamide (Angew. Chem. 76, 807 (1964)) are used in practice in pomiculture and viticulture for combating fungal diseases. N,N-Dimethyl-N'-phenyl-N'-(fluorodichloromethylthio)-sulphamide moreover exhibits an action in the preservation of wood in combating fungi which discolour wood (R. Wegler, Chemie der Pflanzenschutzund Schädlingsbekämpfungsmittel (Chemistry of the Plant Protection Agents and Agents for Combating Pests), Volume 4, page 269 (1977)).

The action of these known compounds, however, is not always satisfactory, especially when low amounts are applied.

New N-sulphenylated carbamic acid esters of the formula

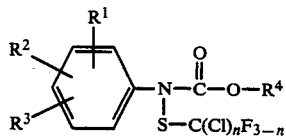

in which $R^1$ to $R^3$ are identical or different and denote hydrogen, halogen, nitro, cyano, alkyl, alkoxy, alkylmercapto, trihalogenomethyl, trihalogenomethoxy or trihalogenomethylmercapto, $R^4$ represents an optionally substituted alkyl, alkenyl, alkinyl, cycloalkyl or aralkyl radical and n represents one of the numbers 0, 1, 2 or 3, have been found.

The new N-sulphenylated carbamic acid esters have an outstanding microbicidal action and are particularly suitable for preserving industrial materials and in plant protection agents.

According to the invention, halogen in general denotes fluorine, chlorine, bromine or iodine, preferably fluorine and/or chlorine.

According to the invention, alkyl in general denotes a straight-chain or branched hydrocarbon radical with 1 to 12, preferably 1 to 8, carbon atoms. Lower alkyl radicals with 1 to about 6 carbon atoms are particularly preferred. The following alkyl radicals may be mentioned as examples: methyl, ethyl, propyl, isopropyl, butyl, isobutyl, pentyl, isopentyl, hexyl and isohexyl.

According to the invention, alkoxy in general denotes a straight-chain or branched hydrocarbon radical which is bonded to oxygen and has 1 to 12, preferably 1 to 8, carbon atoms. Lower alkoxy radicals with 1 to about 6 carbon atoms are particularly preferred. The following alkoxy radicals may be mentioned as examples: methoxy, ethoxy, propoxy, isopropoxy, butoxy, isobutoxy, pentoxy, isopentoxy, hexoxy and isohexoxy.

According to the invention, alkylmercapto in general denotes a straight-chain or branched hydrocarbon radical which is bonded to sulphur and has 1 to 18 carbon atoms. Lower alkylmercapto radicals with 1 to about 6 carbon atoms are particularly preferred. The following alkylmercapto radicals may be mentioned as examples: methylmercapto, ethylmercapto, propylmercapto, isopropylmercapto, butylmercapto, isobutylmercapto, pentylmercapto, isopentylmercapto, hexylmercapto and isohexylmercapto.

According to the invention, trihalogenomethyl in general denotes a methyl radical which is substituted by three identical or different halogen atoms. Halogen here in general denotes fluorine, chlorine, bromine or iodine, preferably fluorine and/or chlorine. The trifluoromethyl group is particularly preferred.

According to the invention, trihalogenomethoxy in general denotes a methoxy radical which is substituted by three halogen atoms. According to the invention, halogen here in general denotes fluorine, chlorine, bromine or iodine, preferably fluorine and/or chlorine. The trifluoromethoxy group is particularly preferred.

According to the invention, trihalogenomethylmercapto in general denotes a methylmercapto radical which is substituted by three halogen atoms. Halogen here in general denotes fluorine, chlorine, bromine or iodine, preferably fluorine and/or chlorine. The trifluoromethylmercapto group is particularly preferred.

According to the invention, alkenyl in general denotes a straight-chain or branched hydrocarbon radical with 2 to 12, preferably 3 to 8, carbon atoms. Lower alkenyl radicals with 3 to about 6 carbon atoms and with one or more, preferably one or two, double bonds are particularly preferred. The following alkenyl radicals may be mentioned as examples: allyl, methallyl, pentenyl and octenyl.

According to the invention, cycloalkyl radicals in general denote cyclic saturated hydrocarbon radicals with 4 to 8, preferably 5 or 6, carbon atoms. The following cycloalkyl radicals may be mentioned as examples: cyclobutyl, cyclopentyl, cyclohexyl, cycloheptyl and cyclooctyl.

According to the invention, aralkyl radicals in general denote aromatic-aliphatic radicals with 7 to 12, preferably 7 to 9, carbon atoms. The following aralkyl radicals may be mentioned as examples: benzyl, 1-phenethyl and 2-phenethyl.

According to the invention, alkinyl in general denotes a straight-chain or branched hydrocarbon radical with 3 to 12, preferably 3 to 8, carbon atoms. Lower alkinyl radicals with one or more, preferably one or two, triple bonds are particularly preferred. The following alkinyl radicals may be mentioned as examples: propargyl, butinyl, hexinyl and octinyl.

The alkyl, alkenyl, alkinyl and cycloalkyl radicals can optionally be substituted by further radicals which do not change under the reaction conditions. The following substituents may be mentioned as examples: alkoxy (C₁ to about C₆), thioalkyl (C₁ to about C₆), N-dialkylamino (in each case C₁ to about C₆), halogen (fluorine, chlorine, bromine or iodine, preferably fluorine and/or chlorine), nitro and cyano. Substituted alkyl, alkenyl, alkinyl and cycloalkyl radicals which may be mentioned in particular are methoxyethyl, methoxymercaptoethyl, isopropoxyethyl, methylmercaptoethyl, N,N-dimethylamino-ethyl, 3-chloropropyl and cyanoethyl.

According to the invention, preferred N-sulphenylated carbamic acid esters are those of the formula

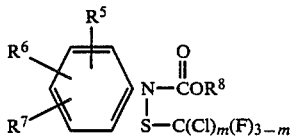

in which
R⁵ to R⁷ are identical or different and denote hydrogen, halogen, nitro, cyano, lower alkyl, lower alkoxy, lower alkylmercapto, trihalogenomethyl, trihalogenomethoxy or trihalogenomethylmercapto,
R⁸ represents alkyl, alkenyl, alkinyl, cycloalkyl or aralkyl, optionally substituted by halogen, cyano, nitro, alkoxy, alkylmercapto or dialkylamino, and
m represents the number 2 or 3.

The following N-sulphenylated carbamic acid esters may be mentioned as examples: N-(trichloromethylsulphenyl) and N-(dichloro-fluoromethylsulphenyl) derivatives of O-methyl, O-isopropyl, O-allyl, O-tert.-butyl, O-isooctyl, O-propargyl, O-methoxyethyl, O-dimethylaminoethyl, O-methylmercaptoethyl, O-cyclohexyl, O-benzyl and O-4-chlorobenzyl N-phenylcarbamate and of ethyl N-(4-chlorophenyl)-, N-(3,5-dichlorophenyl)-, N-(4-trifluoromethylphenyl)-, N-(4-trifluoromethoxyphenyl)-, N-(3-chloro-4-trifluoromethylsulphenylphenyl)- and N-(4-ethoxyphenyl)carbamate.

A process has also been found for the preparation of the new N-sulphenylated carbamic acid esters, which is characterised in that N-substituted carbamic acid fluorides of the formula

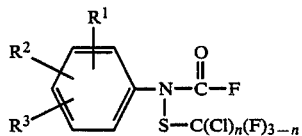

in which
R¹ to R³ and n have the abovementioned meaning, are reacted with an alcohol of the formula

HOR⁴ (IV)

in which
R⁴ has the abovementioned meaning, in the presence of a diluent and an acid-binding agent.

The process according to the invention can be illustrated by the following equation.

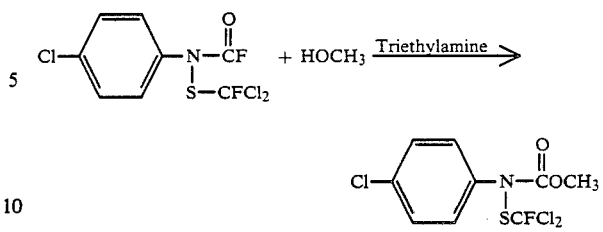

The N-sulphenylated carbamic acid fluorides for the process according to the invention are known per se (German Auslegeschrift No. 1,297,005), and they can be prepared from arylcarbamic acid fluorides and trihalogenomethanesulphenyl chloride in the presence of an acid-binding agent.

Examples which may be mentioned are the N-(trichloromethanesulphenyl)- and N-(fluorodichloromethanesulphenyl)-carbamic acid fluorides of aniline, 2-chloroaniline, 3,4-dichloroaniline, 3-nitroaniline, 4-toluidine, 4-isopropyl-aniline, 4-nitroaniline, 4-toluidine, 4-isopropyl-aniline, 3-chloro-4-methoxyaniline, 2-chloro-4-methyl-mercaptoaniline, 2-chloro-4-trifluoromethylaniline, 4-difluorochloro-methylaniline, 3-chloro-4-trifluoromethoxyaniline and 3-trifluoromethylmercaptoaniline.

The alcohols for the process according to the invention are known per se.

The following alcohols may be mentioned as examples: methanol, ethanol, isopropanol, allyl, alcohol, propargyl alcohol, tert.-butanol, isooctanol, cyclopentanol, cyclohexanol, benzyl alcohol, 3,4-dichlorobenzyl alcohol, methoxyethanol, 2-dimethylaminoethanol and methylmercaptoethanol.

Examples which may be mentioned of diluents for the process according to the invention are: hydrocarbons, such as toluene or xylene, chlorohydrocarbons, such as methylene chloride or chlorobenzene, ethers, such as dioxane, ketones, such as acetone, alcohols, such as ethanol and methanol, or water. Preferred diluents are: hydrocarbons, alcohols and/or water.

Examples which may be mentioned of acid-binding agents for the process according to the invention are: tertiary amines, such as triethylamine, dimethylbenzylamine and pyridine, and inorganic bases, such as sodium hydroxide, sodium carbonate, potassium carbonate, sodium bicarbonate or potassium bicarbonate.

The acid-binding agents are in general employed in an amount of 1 to 2 moles, perferably 1.0 to 1.2 moles, per mole of the N-substituted carbamic acid fluoride.

The process according to the invention can in general be carried out in the temperature range from 0° to 100° C., preferably from 20° to 50° C.

The process according to the invention is in general carried out under normal pressure. However, it is also possible to apply reduced or increased pressures (for example in the pressure range from 0.5 to 1.5 bar).

The process according to the invention can be carried out, for example, as follows:

The N-substituted carbamic acid fluoride is dissolved in a diluent. The alcohol and a tertiary amine are added to this solution and the mixture is stirred at the particular reaction temperature. The reaction product thereby precipitates out, and can be isolated in the customary manner, for example by crystallisation.

The N-substituted carbamic acid esters according to the invention can be used as active compounds for combating undesirable microorganisms, in particular for the preservation of industrial materials and in plant protection.

According to the invention, industrial materials are non-living materials which have been prepared for use in industry. Examples of industrial materials which are to be preserved by the active compounds according to the invention from microbial change or destruction can be adhesives, sizes, paper and card, textiles, leather, wood, paints and articles made of plastics, cooling lubricants and other materials which can be destroyed by microorganisms. Components of production plants, for example cooling water circulations, which can be impaired by microorganisms may also be mentioned in the context of the materials to be preserved. Adhesives, sizes, paper and card, leather, wood, paints, may preferably be mentioned as industrial materials in the context of the present invention.

Examples which may be mentioned of microorganisms which can cause degradation of or a change in the industrial materials are bacteria, fungi, yeasts, algae and slime organisms. The active compounds according to the invention preferably act against fungi, in particular moulds and fungi which discolour and destroy wood (Basidiomycetes), and against slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Staphylococcus, such as *Staphylococcus aureus*, Trichoderma, such as *Trichoderma viride*, Escherichia, such as *Escherichia coli* and Pseudomonas, such as *Pseudomonas areuginosa*.

Depending on the field of application, the active compounds according to the invention can be formulated in the cumstomary manner, for example as a solution, emulsion, suspension, powder, paste or granules.

Formulations of this type can be prepared in a manner which is known per se, for example by mixing the active compounds with an extender which consists of a liquid solvent and/or solid carriers, if appropriate using surface-active agents, such as emulsifiers and/or dispersing agents, it being possible, in the case of the use of water as an extender, for organic solvents, such as alcohols, optionally to be used as auxiliaries.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, or halogenated hydrocarbons, such as 1,2-dichloroethane.

Microbicidal agents in general contain the active compounds in an amount of 1 to 95%, preferably 10 to 75%.

The use concentration of the active compounds according to the invention depends on the nature and occurrence of the microorganisms to be combated, and on the composition of the material to be preserved. The optimum use amount can be determined by test series. In general, the use concentrations are in the range from 0.001 to 5% by weight, preferably 0.05 to 1.0% by weight, based on the material to be preserved.

The active compounds according to the invention can also be in the form of a mixture with other known active compounds. The following active compounds may be mentioned as examples: benzyl alcohol mono(poly)hemiformal and other compounds which split off formaldehyde, benzimidazolyl methylcarbamates, tetramethylthiuramdisulphide, zinc salts or dialkyldithiocarbamates, 2,4,5,6-tetrachloroisophthalonitrile, thiazolylbenzimidazole, mercaptobenzothiazole, trialkyl-tin compounds, methylene bisthiocyanate, 2-thiocyanatomethylthio-benthiazole and phenol derivatives, such as 2-phenylphenol, (2,2'-dihydroxy-5,5'-dichloro)-diphenylmethane and 3-methyl-4-chlorophenol.

The active compounds according to the invention are also suitable for use as plant protection agents, that is to say for protecting living plants. The active compound can be used both in fungicidal and in bactericidal, preferably fungicidal, agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are used in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the Net blotch disease causative organism (*Pyrenophora teres*), against the stripe disease causative organism (*Drechslera graminea*), against Puccinia, Septoria, *Erysiphe graminis* and *Cochliobolus sativus*, and also against the downy mildew of vine causative organism (*Plasmopara viticola*) and against *Pyricularia oryzae* in rice. The broad fungicidal action in the agar plate test and the bactericidal action may furthermore be mentioned. Acaricidal actions are also to be recorded at an appropriate dosage.

The active compounds can be converted to the customary formulations, such as solutions, emulsions, suspensions, powders, foams, pastes, granules, aerosols, very fine capsules in polymeric substances and in coating compositions for seed, as well as ULV formulations (ultra-low volume).

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysation products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

In the treatment of soil, active compound concentrations of 0.00001 to 0.1% by weight, preferably 0.0001 to 0.02%, are required at the place of action.

PREPARATION EXAMPLES

Example 1

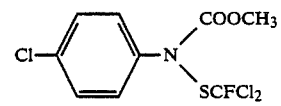

30.6 g (0.1 mole) of N-(4-chlorophenyl)-N-(dichlorofluoromethylsulphenyl)-N-carbamoyl fluoride are dissolved in 100 ml of dioxane with the addition of 8 g (0.26 mole) of methanol. 11 g (0.11 mole) of triethylamine are added dropwise to this solution. During this addition, the temperature is allowed to rise to 35° C. When the reaction has ended, water is added and the oil which separates out is taken up in toluene. After the toluene mixture has been dried and the solvent has been evaporated off, 30 g remain as an oil.

Distillation: boiling point$_{0.1}$ 125° C.; melting point 36°–40° C.; $n_D^{20}$ 1.5548.

The same product is obtained if the reaction is carried out in 100 ml of methanol instead of dioxane.

The products of the Examples 2 to 40 are prepared analogously to Example 1:

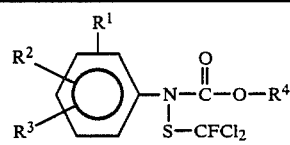

| Example No. | $R^1$–$R^3$ | $R^4$ | Boiling point | Melting point | $(n_D^{20})$ |
|---|---|---|---|---|---|
| 2 | H | CH$_3$ | | 44–45° | |
| 3 | H | i-C$_3$H$_7$ | 105–110°/0.15 | | |
| 4 | H | n-C$_4$H$_9$ | 120–126°/0.2 | | |
| 5 | H | CH$_3$OCH$_2$CH$_2$ | 134–138°/0.02 | | (1.5301) |
| 6 | H | (CH$_3$)$_2$NCH$_2$CH$_2$ | | oily | |
| 7 | H | C$_6$H$_5$—CH$_2$ | 165–168°/0.1 | | |
| 8 | H | 3,4-Cl—C$_6$H$_3$CH$_2$ | | | (1.5853) |
| 9 | 3-Cl | CH$_3$ | | | (1.5591) |
| 10 | 4-Cl | i-C$_3$H$_7$ | | 48° | |
| 11 | 4-Cl | n-C$_4$H$_9$ | 144–151°/0.08 | | (1.5332) |
| 12 | 4-Cl | CF$_3$CH$_2$ | 115–120°/0.1 | | (1.5089) |
| 13 | 4-Cl | CH$_3$OCH$_2$CH$_2$ | 148–152°/0.02 | | (1.5400) |
| 14 | 2,3-Cl | CH$_3$ | | | (1.5631) |
| 15 | 2,3-Cl | i-C$_3$H$_7$ | | | (1.5474) |
| 16 | 2,4-Cl | CH$_3$ | 137°/0.18 | | |
| 17 | 2,4-Cl | i-C$_3$H$_7$ | | | (1.5489) |
| 18 | 3,4-Cl | CH$_3$ | | | |
| 19 | 3,4-Cl | CH$_2$C≡CH | 150–153°/0.1 | | (1.5661) |
| 20 | 3,4-Cl | n-C$_4$H$_9$ | 145–151°/0.1 | | (1.5455) |
| 21 | 3,4-Cl | CH$_3$OCH$_2$CH$_2$ | 168–172°/0.03 | | (1.5520) |
| 22 | 3,5-Cl | CH$_3$ | 135°/0.1 | | |
| 23 | 3,5-Cl | C$_2$H$_5$ | | | (1.5533) |
| 24 | 3,5-Cl | i-C$_3$H$_7$ | | 70–73° | |
| 25 | 3-CH$_3$ | CH$_3$ | 125–130°/0.2 | | |
| 26 | 4-CH$_3$ | CH$_3$ | 127–131°/0.25 | | |
| 27 | 4-CH$_3$ | CCl$_3$CH$_2$ | 160°/0.1 | | |
| 28 | 4-CH$_3$ | CF$_3$CH$_2$ | 130°10.1 | | (1.4946) |

-continued

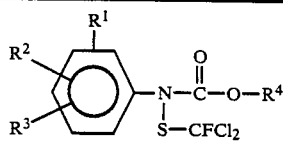

| Example No. | $R^1-R^3$ | $R^4$ | Boiling point | Melting point | $(n_D^{20})$ |
|---|---|---|---|---|---|
| 29 | 2-CH₃, 4-Cl | CH₃ | 126°/0.1 | | |
| 30 | 2-CH₃, 4-Cl | CH₂—C≡CH | 142–145°/0.1 | | |
| 31 | 4-CH₃, 3-Cl | CH₃ | 145–150°/0.2 | | |
| 32 | 3-CF₃ | CH₃ | 94–96°/0.1 | | |
| 33 | 4-CF₃O | CH₃ | 95–100°/0.1 | | (1.5687) |
| 34 | 3-Cl, 4-CF₃ | CH₃OCH₂CH₂ | 146–149°/0.02 | | (1.5070) |
| 35 | 3-Cl, 4-CF₃ | CH₃ | 125–128°/0.1 | | |
| 36 | 3,4-CH₃O | CH₃ | | | (1.5529) |
| 37 | 3,4-CH₃O | i-C₃H₇ | | | (1.5441) |
| 38 | 4-C₂H₅O | CH₃ | 135–140°/0.1 | | |
| 39 | 3,5-Cl, —4CH₃O | CH₃ | | | (1.5600) |
| 40 | 3,5-Cl, —4CH₃O | i-C₃H₇ | | | (1.5445) |
| 40a | 4-Cl | CCl₃CH₂ | | | (1.5642) |

Example 41

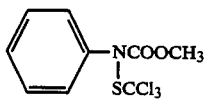

20 g (0.07 mole) of N-phenyl-N-(trichloromethylsulphenyl)-N-carbamoyl fluoride are dissolved in 100 ml of methanol, and 7.8 g (0.077 mole) of triethylamine are added dropwise. During this addition, the temperature rises to 35° C. After customary working up, 9 g of the above product of boiling point$_{0.1}$ 135°–140° C.; melting point 76°–77° C. are obtained by distillation.

Example 42

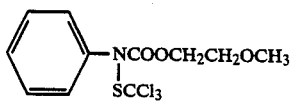

Boiling point$_{0.02}$ 157°–160° C., is prepared analogously to Example 41.

USE EXAMPLES

Example 43

To demonstrate the activity against fungi which destroy industrial materials, the minimum inhibitory concentrations (MIC) of active compounds according to the invention are determined:

Active compounds according to the invention are added in concentrations of 0.1 mg/l to 5,000 mg/l to an agar prepared from bierwort and peptone. After the agar has solidified, it is contaminated with pure cultures of the test organisms listed in the table. After being kept at 28° C. and 60 to 70% relative atmospheric humidity for two weeks, the MIC is determined. The MIC is the lowest concentration of active compound at which no growth at all by the species of microbe used takes place, and is shown in the following Table I.

TABLE I

| | MIC's in mg/l for the action of substances according to the invention on fungi | | | | | | | | |
|---|---|---|---|---|---|---|---|---|---|
| | Substance according to Example | | | | | | | | |
| Test organisms | 41 | 23 | 1 | 9 | 14 | 16 | 18 | 29 | 31 |
| Alternaria tenuis | 0,5 | 5 | | | | | | | |
| Aspergillus niger | 5 | 35 | <20 | <20 | <20 | <20 | 35 | <20 | <20 |
| Aureobasidium pullulans | 1,5 | 3.5 | | | | | | | |
| Chaetomium globosum | 2 | 10 | <20 | <20 | <20 | <20 | <20 | <20 | <20 |
| Coniophora puteana | 0.1 | 1 | | | | | | | |
| Lentinus tigrinus | 0,5 | 1 | | | | | | | |
| Penicillium glaucum | 20 | 7.5 | <20 | <20 | <20 | <20 | <20 | <20 | <20 |
| Polyporus versicolor | 1,5 | 2 | | | | | | | |
| Sclerophoma pityophila | 1 | 1.5 | | | | | | | |

Example 44

*Pyrenophora teres* test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

TABLE II

Pyrenophora teres test (barley)/protective

| Active compound | Active compound concentration in the spray liquor in % by weight | Disease infestation in % of the untreated control |
|---|---|---|
| known: | | |
| (CH₃)₂N—SO₂NSCCl₂F (with phenyl group) | 0.025 | 72.5 |
| according to the invention: | | |
| Cl, H₃C-phenyl-N(SCFCl₂)—COOCH₃ | 0.025 | 39.4 |
| Cl, Cl-phenyl-N(SCFCl₂)—COOCH₃ | 0.025 | 37.7 |
| CH₃, Cl-phenyl-N(SCFCl₂)—COOCH₃ | 0.025 | 31.3 |
| CF₃-phenyl-N(SCFCl₂)—COOCH₃ | 0.025 | 30.3 |
| Cl, Cl-phenyl-N(SCFCl₂)—COOCH₃ | 0.025 | 30.3 |
| Cl-phenyl-N(SCFCl₂)—COOCH₃ | 0.025 | 20.3 |
| Cl, F₃C-phenyl-N(SCFCl₂)—COOCH₃ | 0.025 | 20.3 |
| phenyl-N(SCCl₃)—COOCH₃ | 0.025 | 20.3 |
| H₅C₂O-phenyl-N(SCFCl₂)—COOCH₃ | 0.025 | 29.4 |
| Cl, H₃CO, Cl-phenyl-N(SCFCl₂)—COOCH₃ | 0.025 | 25.0 |

TABLE II-continued
Pyrenophora teres test (barley)/protective

| Active compound | Active compound concentration in the spray liquor in % by weight | Disease infestation in % of the untreated control |
|---|---|---|
| Cl, H₃CO, Cl-phenyl-COO—i-C₃H₇ (SCFCl₂) | 0.025 | 25.0 |
| H₃CO, H₃CO-phenyl-N(SCFCl₂)—COOCH₃ | 0.025 | 0.0 |
| H₃CO, H₃CO-phenyl-COO—i-C₃H₇ (SCFCl₂) | 0.025 | 25.0 |
| Cl-phenyl-N(SCFCl₂)—COOCH₂CCl₃ | 0.025 | 33.7 |
| Cl, Cl-phenyl-N(SCFCl₂)—COOCH₃ | 0.025 | 14.5 |
| Cl-phenyl-N(SCFCl₂)—COOCH₃ | 0.025 | 37.7 |

Example 45

Drechslera graminea test (barley)/seed treatment (syn. Helminthosporium gramineum)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

TABLE III
Drechslera graminea test (barley)/seed treatment (syn. Helminthosporium gramineum)

| Active compound | Amount of active compound applied in mg/kg of seed | Diseased plants in % of the total plants emerged |
|---|---|---|
| undressed | — | 29.7 |
| known: | | |

TABLE III-continued

Drechslera graminea test (barley)/seed treatment
(syn. *Helminthosporium gramineum*)

| Active compound | Amount of active compound applied in mg/kg of seed | Diseased plants in % of the total plants emerged |
|---|---|---|
| $(CH_3)_2N-SO_2NSCCl_2F$ with phenyl on N | 600 | 23.9 | according to the invention:

| Active compound | Amount | % |
|---|---|---|
| 3-Cl, 4-CH_3-phenyl-N(SCFCl_2)-COOCH_3 | 500 | 3.2 |
| 2-CH_3, 4-Cl-phenyl-N(SCFCl_2)-COOCH_3 | 500 | 0.0 |
| 3-CF_3-phenyl-N(SCFCl_2)-COOCH_3 | 500 | 0.0 |
| 3,5-Cl_2-phenyl-N(SCFCl_2)-COOCH_3 | 500 | 0.0 |
| 3-Cl, 4-CF_3-phenyl-N(SCFCl_2)-COOCH_3 | 500 | 1.0 |
| phenyl-N(SCFCl_2)-COOCH_3 | 500 | 3.1 |

Example 46

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

TABLE IV

Pyricularia test (rice)/protective

| Active compound | Active compound concentration in % | Disease infestation in % of the untreated control |
|---|---|---|
| known: | | |
| $CH_2-NH-CS-S$ / $CH_2-NH-CS-S$ Zn | 0.025 | 75 |
| according to the invention: | | |
| phenyl-N(SCFCl_2)-COOCH_2CH_2OCH_3 | 0.025 | 30 |
| phenyl-N(SCFCl_2)-COOCH_2-phenyl | 0.025 | 0 |
| 3,4-Cl_2-phenyl-CH_2OC(O)-N(SCFCl_2)-phenyl | 0.025 | 10 |

Example 47

Plasmopara test (vines)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

TABLE V

Plasmopara test (vines)/protective

| | Infestation in % at an active compound concentration of | |
|---|---|---|
| Active compound | 2 ppm | 1 ppm |
| known: | | |
| phthalimide-N-SCCl_3 | 62 | 73 |
| according to the invention: | | |

TABLE V-continued

Plasmopara test (vines)/protective

| Active compound | Infestation in % at an active compound concentration of | |
|---|---|---|
| | 2 ppm | 1 ppm |
| 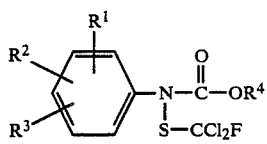 | 24 | 47 |

What is claimed is:

1. A N-sulphenylated carbamic acid ester of the formula

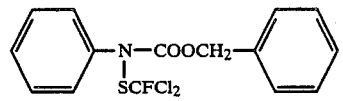

in which

R¹ to R³ are identical or different and denote hydrogen, chloro or methyl and,

R⁴ represents methyl.

2. A carbamic acid ester according to claim 1 of the formula

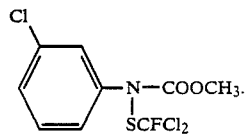

3. A carbamic acid ester according to claim 1 of the formula

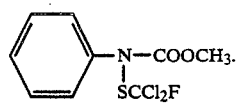

4. A carbamic acid ester according to claim 1 of the formula

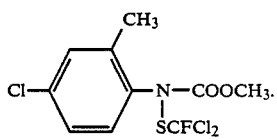

5. A carbamic acid ester according to claim 1 of the formula

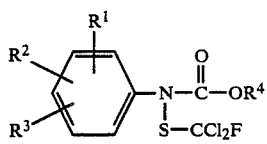

* * * * *

UNITED STATES PATENT AND TRADEMARK OFFICE
CERTIFICATE OF CORRECTION

PATENT NO. : 4,798,905
DATED : January 17, 1989
INVENTOR(S) : Engelbert Kühle, et al It is certified that error appears in the above-identified patent and that said Letters Patent is hereby corrected as shown below:

| | |
|---|---|
| Col. 4, line 32 | Delete "allyl, alcohol" and substitute --allyl alcohol-- |
| Col. 8, Example No. 12 under ($n_D^{20}$) | Delete "(1.5089)" and substitute --1.5069)-- |
| Col. 8, Example No. 28 under Boiling Point | Delete "130°10.1" and substitute --130°/0.1-- |
| Col. 8, Example No. 28 | Move "(1.4946)" from under "Melting Point" to under "($n_D^{20}$)" |
| Col. 9-10, Table I, under "41" | First line delete "0,5" and substitute --0.5--; third line delete "1,5" and substitute --1.5--; sixth line delete "0,5" and substitute --0.5--; eighth line delete "1,5" and substitute --1.5-- |

Signed and Sealed this

Tenth Day of October, 1989

Attest:

DONALD J. QUIGG

Attesting Officer

Commissioner of Patents and Trademarks